United States Patent

Bare et al.

[11] Patent Number: 6,103,721
[45] Date of Patent: Aug. 15, 2000

[54] HETEROARYL-SUBSTITUTED PYRIDAZINO QUINOLINE COMPOUNDS

[75] Inventors: Thomas Michael Bare, West Chester, Pa.; Timothy Wayne Davenport, New Castle; James Roy Empfield, Bear, both of Del.; Jeffrey Alan McKinney, Palo Alto, Calif.; Richard Bruce Sparks, Linwood, Pa.

[73] Assignee: Zeneca Limited, United Kingdom

[21] Appl. No.: 09/455,096

[22] Filed: Dec. 6, 1999

Related U.S. Application Data

[62] Division of application No. 09/044,109, Mar. 19, 1998, which is a division of application No. 08/637,641, filed as application No. PCT/GB94/02295, Oct. 20, 1994, Pat. No. 5,744,471.

[30] Foreign Application Priority Data

Oct. 22, 1993 [GB] United Kingdom .................... 9321854
Aug. 25, 1994 [GB] United Kingdom .................... 9417171

[51] Int. Cl.$^7$ ..................... A61K 31/5025; C07D 471/04
[52] U.S. Cl. ............................................ 514/248; 544/234
[58] Field of Search .............................. 544/234; 514/248

[56] References Cited

U.S. PATENT DOCUMENTS

| | | | |
|---|---|---|---|
| 5,599,814 | 2/1997 | Bare et al. ............................... | 544/234 |
| 5,604,227 | 2/1997 | Bare et al. ............................... | 544/234 |
| 5,744,471 | 4/1998 | Bare et al. ............................... | 514/248 |
| 5,837,705 | 11/1998 | Bare et al. ............................... | 514/248 |

FOREIGN PATENT DOCUMENTS

| | | |
|---|---|---|
| 512817 | 11/1992 | European Pat. Off. . |
| 516297 | 12/1992 | European Pat. Off. . |
| 9615127 | 5/1996 | WIPO . |

OTHER PUBLICATIONS

Kurasawa et al., Heterocycles, 14(3), 267–270 (1980).
Luo et al., J. Heterocyclic Chemistry, 28, 205–208 (1991).
Tominaga et al., J. Heterocyclic Chemistry, 30, 267–273 (1993).
Kurasawa et al., Chem. Pharm. Bull., 28(12), 3457–3465 (1980).
Godard et al., Bull. Soc. Chim. Fr., 1588–1592 (1972).
Ried et al., Chem. Ber., 85, 204–216 (1952).
Choi, Neuron 1, p 623–634 (1988).
Koh et al., Brain Research, 533, p 315–320 (1990).
Trujillo et al., Science, 251, p 85–87 (1991).

*Primary Examiner*—Emily Bernhardt
*Attorney, Agent, or Firm*—Kenneth F. Mitchell

[57] ABSTRACT

The present invention concerns compounds according to the following formula,

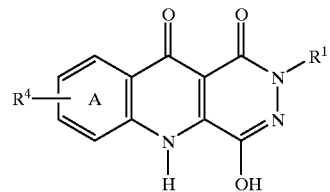

wherein: $R^1$ is $(CH_2)_n L$ where n is an integer in the range 0 to 6, and L is a carbon-linked five-membered heteroaryl ring having an oxygen or sulfur heteroatom, $R^4$ is hydrogen, halo or $NO_2$, and pharmaceutical compositions and methods of using thereof in the treatment and/or prevention of neurological diseases or conditions.

9 Claims, No Drawings

HETEROARYL-SUBSTITUTED PYRIDAZINO QUINOLINE COMPOUNDS

This is a division of application Ser. No. 09/044,109, filed Mar. 19, 1998, which is a division of application Ser. No. 08/637,641, now U.S. Pat. No. 5,744,471, which is a § 371 filing of PCT/GB94/02295, filed Oct. 20, 1994.

FIELD OF THE INVENTION

This invention relates to compounds generally useful in the treatment of neurological disorders in mammils such as man. Particularly, this invention relates to pyridazinedione compounds useful in reducing neurological degeneration such as is induced by a stroke and to reducing the associated functional impairment which can thereby result.

RELATED ART

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites iiln brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

EPO publication number 0 516 297 Al describes certain pyridazinediones. In addition, the compounds thieno[2', 3':5,6]pyrido[2,3-d]pyridazine-5,8,9(4H,6H,7H)-trione and thieno[3', 2':5,6]pyrido[2,3-d]pyridazine-4,5,8(6H,7H,9H)-trione are known from J. Heterocyclic Chern., 28, 205, (1991). Other pyridazinedione compounds are also known from, for example from Beilstein's Handbuch der Organischen Chemie; Godard et. al., Bull. Soc. Chim. Fr., 1588, (1972); and Reid et. al., Chem. Ber., 85, 204, (1952).

SUMMARY OF THE INVENTION

The present invention provides compounds and pharmaceutical compositions thereof suitable for the treatment of neurological disorders.

Compounds of the present invention are substituted pyridazinediones or pharmaceutically-acceptable salts thereof of formula I

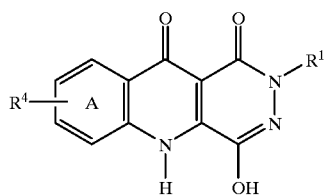

wherein:

$R^1$ is $(Ch_2)_nL$, where n is an integer in the range 0 to 6 and L is a carbon-linked five-membered heteroaryl ring having an oxygen or sulfur heteroatom, and $R^4$ at each cccurrence is independently selected from hydrogen, halo and $NO_2$, and ring-A has four $R^4$ groups.

In particular compounds of the present invention, $R^1$ is $CH_2$-L where L is selected from 2-linked or 3-linked furanyl or thiophenyl moieties and $R^4$ is hydrogen or halo, and ring-A has 7-linked halo or 7,9-linked di-halo groups.

More particularly $R^1$ is $CH_2$-L where L is selected from 2-linked or 3-linked furanyl or thiophenyl moieties and $R^4$ is hydrogen or chloro, and ring-A has a 7-linked chloro or 7,9-linked di-chloro groups.

Most particularly compounds of formula I of the present invention are selected from 7-chloro-4-hydroxy-2-(furan-2-ylmethyl)-1,2,5,10-tetrahydropyridazino[4,5-b]quinolin-1,10-dione, 7-chloro-4-hydroxy-2-(furan-3-ylmethyl)-1,2,5,10-tetrahydropyridazino [4,5-b]quinolin-1,10-dione, 7-chloro-4-hydroxy-2-(thiophen-2-ylmethyl)-1,2,5,10-tetrahydropyridazino [4,5-b]quinolin-1,10-dione, and 7-chloro-4-hydroxy-2-(thiophen-3-ylmethyl)-1,2,5,10-tetrahydropyridazino [4,5-b]quinolin-1,10-dione Thus, according to the invention, there is provided compounds of formula I, tautomers thereof and, together with pharmaceutically-acceptable diluents or carriers, pharmaceutical compositions thereof suitable for the treatment of neurological disorders.

The invention further provides a method for the treatment of neurological disorders, that comprises administering to a mammal suffering from such a disorder an effective amount of a compound according to the invention as defined above, or a pharmaceutically-acceptable salt thereof, or a composition as defined above.

The invention also encompasses a method of antagonizing an NMDA receptor in mammals comprising administering a pharmaceutically-effective amount of the compound or its salt as claimed herein or a pharmaceutical composition as recited herein to a patient. A particular therape-tic treatment area is the prevention and/or treatment of stroke. A pharmaceutically- effective amount of a compound as claimed and disclosed in the present invention may be administered immediately after an ischemic event to prevent cell damage and/or cell death.

The preselnt invention is also directed to a method of preventing and/or treating damage induced by the excitatory amino acids such as L-glutamate.

Further, the invention also relates to a method of preventing the excessive influx of calcium ions in c(lentral neurons by administering a pharmaceutically-effective amount of a compound of formula I.

Still furthler, the invention further relates to a method of preventing ischemic neuronal injury following lTransient global ischemia and a method of reducing infarct volume following focal ischemic insults by treating a patient suffering therefrom with a pharmaceutically-effective amount of a compound of formula I.

Yet further, in addition to being useful in the treatment of acute stroke patients, the compounds and compositions of the invention may be extremely beneficial in preventing neurological morbidity during cardiac resuscitation or be administered as cerebral prophylatics during high-risk surgery.

DETAILED DESCRIPTION OF THE INVENTION

The inventLon disclosed herein is disclosed in the commonly-owned parent of this application, U.S. Pat. No. 5,744,471, the disclosure of which is incorporated herein by reference in its entirety.

As used herein, the term "halo" encompasses fluoro, chloro, bromo, and iodo unless noted otherwise.

As used herein the term "heteroaryl" encompasses tetrazole, furan, thiophene, diazole, imidazole, triazole, pyridine, pyrimidine, pyridazine or pyrazine.

The particular values for the $R^1$ and $R^4$ designated values of formula I, include those values or groups which are specifically exemplfied in the examples and schemes.

Particular values of $R^4$ include hydrogen, fluoro, chloro, bromo, iodo and nitro.

Compounds of the present invention are substituted pyridazinediones or pharmaceutically-acceptable salts thereof of formula I as disclosed heretofore wherein:

$R^1$ is $(CH_2)_nL$, where n is an integer selected from 0, 1, 2, 3, 4, 5 or 6 and L is a carbon-linked five-membered heteroaryl ring having an oxygen or sulfur heteroatom, and $R^4$ at each occurrence is independently selected from hydrogen, halo and $NO_2$, and ring-A has four $R^4$ groups.

In particular compounds of the present invention, $R^1$ is $CH_2$-L where L is selected from 2-linked or 3-linked furanyl or thiophenyl moieties and $R^4$ is hydrogen or halo, and ring-A has 7-linked halo or 7,9-linked di-halo groups.

More particularly $R^1$ is $CH_2$-L where L is selected from 2-linked or 3-linked furanyl or thiophenyl moieties and $R^4$ is hydrogen or chloro, and ring-A has a 7-linked chloro or 7,9-linked di-chloro groups.

Particular compounds of formula I of the present invention include: 7-chloro-4-hydroxy-2-(furan-2-ylmethyl)-1,2,5,10-tetrahydropyridazino[4,5-b]quinolin-1,10-dione; 7-chloro-4-hydroxy-2-(furan-3-ylmethyl)-1,2,5,10-tetrahydropyridazino[4,5-b]quinolin-1,10-dione; 7-chloro-4-hydroxy-2-(thiophen-2-ylmethyl)-1,2,5,10-tetrahydropyridazino [4,5-b]quinolin-1,10-dione, and 7-chloro-4-hydroxy-2-(thiophen-3-ylmethyl)-1,2,5,10-tetrahydropyridazino[4,5-b]quinolin-1,10-dione, and pharmaceutically-acceptable salts thereof.

Treatment using a compound of the invention can be remedial or therapeutic as by administering a co)mpound following an ischemic event to mitigate the effects of that event. Treatment can allh o be prophylactic or prospective by administering a compound in anticipation that lan ischemic event may occur, for example in a patient undergoing surgery or who is prone to stroke. Compounds of the present invention are useful in the treatment of strokes and neurolclegenerative disorders that result from such causes as hypoglycemia, cerebral palsy, transient cerebral ischemic attack, perinatal asphyxia, epilepsy, psychosis, Huntington's chorlna, amyotrophic lateral sclerosis, Alzheimer's disease, Parkinson's disease, Olivo-pontocerebellar atrophy, viral-induced neurodegeneration such as in acquired immunodeficiency, syndrome and its associated dementia, anoxia such as from drowning, spinal cord and brain trauma.

Compounds of the present invention may be useful in a variety of neurodegenerative disorders because they function as excitatory amino acid antagonists. Such compounds may function indirectly, via allosteric modulation of the glutamate binding site, particularly by acting as antagonists of the strychnine-insensitive glycine receptor on the NMDA receptor complex. Compounds of the present ivention may also function directly by binding to the glutamate site itself on the NMDA receptor complex.

Pyridazinediones of formula I can be made by processes which include processes known in the chemical arts for the production of structurally analogous compounds. The preparation of corlapounds can be affected by chlorinating the hydroxy group of a dialkyl-4-hydroxyquinolin-2,3-dicarboxylate starting material using phosphorous oxychloride. The chlorine is then reduced using tetrakistriphenylphosphine Pd(O) and sodium formate to provide N-dimethylquinolin-2,3-dicarboxylate which is then processed through other chemical steps such as adding the hydrazine. The processes for the manufacture of a pyridazinedione of formula I as defined above can be effected, generally, as disclosed in U.S. Pat. No. 5,744,471 the subject matter of which is incorporated by reference in its entirely.

It will be la,Lppreciated that compounds of formula I of this invention that contain asymmetrically substituted carbon atoms may exist in, and be isolated in, optically-active and racemic forms. In addition, compounds of formula I, for example those containing a double bond, may exist in stereoisomeric forms, and may be individually isolated. Further, it will be appreciated that slo)me compounds may exhibit polymorphism. It is to be understood that the present invention encompasses any racemic, optically-active, polymorphic or stereoisomeric form, or mixtures thereof. It will be appreciated that it is well known in the art how to prepare optically-active forms, for example by resolution of a racemic mixture or by synthesis from optically-active starting materials.

Examples of pharmaceutically-acceptable salts are salts formed with bases which form a physiologically-acceptable cation, such as an alkali metal ion, for example lithium, sodium and potassium or an alkaline-earth metal ion, for example, calcium and magnesium. Other pharmaceutically-acceptable salts are aluminum and ammonium salts, as well as salts made with appropriate organic bases such as choline hydroxide, triethylamine, morpholine, piperidine, ethylenediamine, lysine, ethanolamine, diethanolamine, triethanolamine, N-methyl-D-glucamine (meglumine), arginine, and tris(hydroxymethyl)aminomethane. Particularly suitable salts are choline, meglumine, sodium and potassium salts.

When useld to intervene therapeutically following a stroke, a pyridazinedione of formula I generally is administered as an appropriate pharmaceutical composition which comprises a compound according to the invention as defined hereinbefore together with a pharmaceutically-acceptable diluent or carrier, the composition being adapted for the particular route olf administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; and in the form of powders together with pharmaceutically-acceptable inert solid diluents such as lactose for administration by insufflation.

The dose of a compound according to the invention which is administered will necessarily be varied according to principles well known in the art taking account of the route of administration, the severity of the postischemic disorder, and the size and age of the patient. In general, a compound of according to the invention will be administered to a warm blooded animal (such as man) so that an effective dose is received, generally a dose in the range of about 0.01 to about 100 mg/kg body weight. For example, if the compound is administered intravenously, it is administered in the range of about 0.01 to about 10 mg/kg body weight. If it is administered orally, it is administered in the range of about 0.5 to about 100 mg/kg body weight. The preferred route of administration is intravaneously.

It will be apparent to those skilled in the art that a compound according to the invention can be co-administered with other therapeutic or prophylactic agents and/or medicaments that are not medically incompatible therewith.

The action, of compounds according to the invention as antagonists at the glycine receptor of the NNIDA receptor complex can be shown by one or more standard tests such as the [³H]-glycine binding assay (Test A) and by tests in vivo such as ischemia induced by carotid occlusion in the gerbil model (Test B). In addition to these tests, compounds of the invention are assaied in the red nucleus test (Test C) and in the Rat Middle Cerebral Artery test (Test D). Thelre tests confirm that compounds of the invention are NMDA receptor antagonists in vitro and in vivo. Compounds of the present invention are potent NMDA receptor antagonists. In particular, the compounds of the present invention with $R^1$ as an alkyl, aryl or heteroaryl moiety as defined herein are potent NMDA receptor (Glycine) antagonists.

Biological Tests:

Test A: [³H]-glycine Binding Assay

In the [³H]-glycine binding assay, neuronal synaptic membranes are prepared from adult (about 250 g) male Sprague-Dawley rats. Freshly dissected cortices and hippocampi are homogenised in 0.32 M sucrose (110 mg/mL). Synaptosomes are isolated by centrifugation (1000 xg, 10 min.), the supernatant is pelleted (20,000 xg, 20 min) and resuspended in double-distilled water. The suspension was centrifuged for 20 minutes at 8,000 xg. The resulting supernal ant and buffy coat are washed twice (48,000 xg, 10 mins, resuspension in double-deionized water). The final pellet is quickly frozen (dry ice/ethanol bath) under double-deionized water and stored at −70° C.

On the day of the experiment, thawed synaptic membranes are homogenized with a Brinkmann Polytron (tm, Brinkmann Instruments, Westbury, N.Y.) tissue homogenizer in 50 millimolar tris(hydroxymethyl)aminomethane citrate, pH 7.1. The membranes are incubated with 0.04% Sufact-AMPS X100 (tm, Pierce, Rockford, Ill.) in buffer for 20 minutes at 37° C. and washed six times by centrifugation (48,000 xg, 10 min) and resuspended in buffer. The final pellet is holmlrogenized at 200 mg wet weight/mL of the buffer for the binding assay.

For [³H]-glycine binding at the N-methyl-D-aspartate receptor, 20 nanomolar [³H]-glycine (40–60 Ci/mmol, New England Nuclear, Boston, Mass.) is incubated with the membranes suspended in 50 millimolar tris (hydroxymethyl)aminomethane citrate, pH 7.1 for 30 minutes at 4° C. Glycine, 1 millimolar, is used to define the non-specific binding. Bound [³H]-glycine is isolated from the free form using a Brandel (Biomedical Research and Development Laboratories, Gaithersburg, Md.) cell harvester for vacuum filtration over glass fibre filters (Whalman GF/B from Brandel, Gaithersburg, Md.) pre-soaked in 0.025% polyethyleninine. The samples retained on the glass fibre filters are rinsed 3 times with a total of 2.5 mL ice cold buffer. Radioactivity is estimated by liquid scintillation counting. $IC_{50}$ values are obtained from a least-squares regression of a logit-log transformation of the data. $IC_{50}$ values for exemplary compounds of this invention are for Example 1 ($IC_{50}$ 0.014 μM), Example 2 ($IC_{50}$ 0.151 μM), Example 3 ($IC_{50}$ 0.035 μM) and for Example 4 ($IC_{50}$ 0.111 μM).

Test B: Glerbil Ischaemic Model

When testing in vivo using the gerbil ischaemic model, adult female Mongolian gerbils (50–70 g) are anaesthetised with 2 to 3% halothane. The bilateral common carotid arteries at the neck are exposed and occluded with microaneurysm clips. After 10 min (unless otherwise specified), the clil)s are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped. Gross behavioural observations along with motor activity are recorded for 2 hr on the first (24 hr) day following the occlusion. After 4 days, subjects are sacrificed (decapitation), brains are removed, fixed, sectioned and stained with hematoxylin/eosin and cresyl violet.

The brain sections are rated for neuronal damage in the hippocampus using the following rating scale:

0=undalraged, normal

1=slight damage (up to 25%)—restricted to CAl/subiculum border

2=moderate damage (up to 50%)—obvious damage, restricted to less than half of CA1 field 3=marked damage (up to 75%)—involving greater than half of CA1 field 4=damage extending beyond CA1 field Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxon-Rank Sum test.

Compounlds of the invention are tested according to the above regimen by intraperitoneal (ip) administration at a level of 10 mg/Kg body weight.

Test C: Red Nucleus Test

This test determines the effects of intravenously administered glycine antagonists on the NMDA-induced excitatory response of red nucleus cells. HA-966 (racemic) and CGP 37849 are reference agents that have been shown to be active in this test and to have $ID_{50}$s of 7.9 and 1.7 mg/kg iv, respectively.

The procedure for the red nucleus test is as follows. Rats are anaesthetised with chloral hydrate (400 mg/kg ip) and the femoral vein is catheterised for iv drug administration. Five-barrel micrcpipettes are stereotaxically positioned in the red nucleus. Typically, three to four of the five barrels are filled as follows: the recording barrel with 2 M potassium citrate, the current balancing barrel with 4M NaCl, the drug barrel with 25 mM NMDA, and another drug barrel with 2.5 mM quisqualic acid (QA is only used in selectivity studies). NMDA is iontophoretically ipplied with an ejection current that is adjusted depending on the sensitivity of each individual red nucleus cell. The NMDA is cycled on and off (usually 30–60 sec. on and 60–120 sec. off) and the firing rate of the cell during each period is recorded. Once the baseline firing rat(le of the cell has been established, the test drug is administered iv. The effect of the drug on the NMDA-induced excitatory response of the red nucleus cell can be both qualitatively and cquantitatively evaluated from the recordings and the raw data accumulated. Compounds of the invention exhibited a significant antagonist response.

Results for the red nucleus assay: Example 1 $ID_{50}$=2.8 mg/kg, i.v.; Example 2 $ID_{50}$=9.5 mg/kg, i.v.; Example 4 $ID_{50}$=4.9 mg/kg, i.v.

Test D: Rat Middle Cerebral Artery Test

Male SHR rats weighing 280–320 g are used for these studies. The method used for permanent middle cerebral artery (MCA) occlusion is as described by Brint et al ., J. Cerebral Blood Flow (1988) 8, 474–485. Briefly, focal ischaemia is produced by occluding first the left common carotid artery and then the left middle cerebral artery just superior to the rhinal fissure. Following occlusions, drugs are administered intravenously via jugular catheter. Twenty-four hours after MCA/common carotid artery occlusion, the animals are sacrificed and their brains quickly removed. Coronal sections of 1 mm thickness are cut using a vibratome and stained with 2,3,5-triphenyl-2H-tetrazolium chloride (TTC) dye. Following staining, necrotic tissue is readily distinguished from the intact brain and the area of infarcted cortex can be trac:ed on an image analyzer. The infarct volume for each section is quantified with an image analyzer, and the total infarct volume is calculated with a program that summed all interval volume. See S. Brint et al., (1988). The statistical analysis of the difference between the volume of ischemic damage in the vehicle control and drug-treated animals is analysed by student's-t-test. All data are presented as the mean ± S.E. of the mean for n animals. Compoluinds of the present invention reduced ischemic damage as follows: compound of ExlaLmple 1 gave 17% protection when administered as 20 mg/kg bolus followed by 20 mg/kg/hr for 4 hr; compound Example 2 gave 26% protection when administered as 10 mg/kg bolus followed by 10 mg/kg/hr for 4 hr; compound of Example 3 gave 27% protection when administered as 15 mg/kg bolus followed by 15 mg/kg/hr for 4 hr, and compound of Example 4 gave 13% protection when administered as 15 mg/kg bolus followed by 15 mg/kg/hr for 4 hr The present invention is illustrated by the following non-limiting examples.

The abbreviations that follow are used in the following examples, unless stated otherwise:

(i) temperatures are given in degrees Celsius (° C.); operations were carried out at room or ambient temperature, that is, at a temperature in the range of 18–25° C.;

(ii) evaporation of solvent was carried out using a rotary evaporator under reduced pressure (600–4000 Pascals; 4.5–30 mm Hg) with a bath temperature of up to 60° C.;

(iii) flash chromatography was carried out on Merck Kieselgel (Art 9385) and column chromatography cn Merck Kieselgel 60 (Art 7734) obtainable from E. Merck, Darmstadt, W. Germany; thin layer chromatography (TLC) was carried out on Analtech 0.25 mm silica gel GHLF plates (Art 21521) obtainable from Analtech, Newark, Del., USA;

(iv) in general, the course of reactions was followed by TLC or HPLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC or HPLC and had satisfactory nuclear magnetic r esonance (NMR) spectra (300 MHz $^1$H NMR in D-DMSO unless otherwise specified) and microanalytical data;

(vii) yields are given for illustration only;

(viii) reduced pressures are given as absolute pressures in Pascals (Pa); other pressures are given as gauge pressures in bars;

(ix) chemical symbols have their usual meanings; the following abbreviations have also been used: v (volume), w (weight); m.p. (melting point), L [liter(s)], mL (milliliters), mM (millimoles), g [gram(s)], mg [milligram(s)], min (minutes), h (hour); and (x) solvent ratios are given in volume/volume (v/v) terms.

EXAMPLES

The following Examples correspond to the examples of the parent application, now U.S. Pat. No. 5,741,471, as follows: 1/115, 2/140, 3/141, 4/142, 5/145, 6/146, 7/147 and 8/148.

Example 1:

7-chloro-4-hydroxy-2-(thiophen-2-yl-methyl)-1,2,5,10-tetrahydropyridazino 4,5-b]quinolin-1,10-dione To a solution of 2-(thiophen-2-yl-methyl)-t-butylcarbazate (1.0 g, 4.4 mM) and 2-pyrrolamido-3-carboxy-7-chloroquinolin-4-one (1.2 g, 3.6 mM) in tetrahydrofuran (75 mL) stirred at room temperature, was added diisopropylcarbodiimide (0.84 mL, 5.4 mM). This mixture was stirr(,d at room temperature for 2.5 hours, then suction filtered into a second reaction flask. To the filtrate (stirred at room temperature) was added methanesulfonic acid (12 mL, 185 mM). The resulting solution was stirred 17 hours at room temperature. TLC analyses at this time indicated complete reaction. The reaction mixture was poured into ice water (200 mL). This suspension was stirred about 15 minutes and filtered. The filter cake was washed with water and ether, then vacuum dried to yield the analytically pure desired compound (1.1 g, 84%). m.p.>250° C.; NMR (DMSO -$d_6$) 360(M+1) 5.23(s, 2H), 6.98(m, 1H), 7.10(m, 1H), 7.43(m, 2H), 8.02(d, 1H, J=1.95Hz), 8.14(d, 1H, J=8.7Hz), 11.92(brs, 1H), 12.7(brs, 1H); Analysis for $C_{16}H_{10}C1N_3O_3S$-0.5$H_2O$, calc./found: C=52.11/52.10, H=3.01/3.32, N=11.39/11.10.

Example 2:

7-chloro-4-hydroxy-2-(furan-2-ylmethyl)-1,2,5,10-tetrahydropyridazino [4,5-b]quinolin-1,10-dione 7-chloro-4-hydroxy-2-(furan-2-ylmethyl)-1,2,5,10-tetrahydropyridazino [4,5-b]quinolin-1,10-dione was prepared as described in Example 1 from a solution of 2-(furan-2-yl-methyl)-t-butylcarbazate. Yield 51%, m.p. >250° C.; NMR (DMSO -$d_6$), 344(M+1) 5.09(s, 2H), 6.36 (d, 1H, J=3.1Hz), 6.42(m, 1H), 7.42(m, 1H), 7.59(d, 1H, J=1.0Hz), 8.02(d, 1H, J=1.9Hz), 8.14(d, 1H, J=8.7Hz), 11.9 (brs, 1H), 12.7(brs, 1H); Analysis for $C_{16}H_{10}C1N_3O_4$ — 0.2$H_2O$, calc./found: C=55.46/55.33, H=3.12/3.02, N=11.39/11.10.

Example 3:

7-chloro-4-hydroxy-2-(thiophen-3-ylmethyl)-1,2,5,10-tetrahydropyridazino [4,5-5 b]quinolin-1,10-dione 7-chloro-4-hydroxy-2-(thiophen-3-ylmethyl)-1,2,5,10-tetrahydropyridazino [4,5-b]quinolin-1,10-dione was prepared as described in Example 1 from a solution of 2-(thiophen-3-yl-methyl)-t-blutylcarbazate. Yield 65%; m.p. >250° C.; NMR (DMSO -$d_6$), 360(M+1) 5.08(s, 1H), 7.08 (d, 1H, J=4.86Hz), 7.37(s, 1H), 7.43(d, 1H, J=8.6Hz), 7.50 (m, 1H), 8.02(s, 1H), 8.14(d, 1H, J=8.6Hz), 11.92(brs, 1H), 12.65(brs, 1H); Analysis for $C_{16}H_{10}C1N_3O_3S$ —0.2$H_2O$, calc./found: C=52.88/52.91, H=2.88/3.12, N=11.56/11.35

Example 4:

7-chloro-4-hydroxy-2-(furan-3ylmethyl)-1,2,5,10-tetrahydropyridazino[4,5-b]quinolin-1,10-dione 7-chloro-4-hydroxy-2-(furan-3-ylmethyl)-1,2,5,10-tetrahydropyridazino [4,5-b]quinolin-1,10-dione was prepared as described in Example 1 from a solution of 2-(furan-3-yl-methyl)-t-butylcarbazate. Yield 59%; m.p. >250° C.; NMR (DMSO -$d_6$),344(M+1) 4.92(s, 1H), 6.46(s, 1H), 7.43(d, 1H, J=8.46Hz), 7.63(m, 1H), 8.02(d, 1H, J=1.6), 8.14(d, 1H, J=8.61Hz), 11.92(brs, 1H), 12.67(brs, 1H); Analysis for $C_{16}H_{14}C1N_3O_4$, calc./found: C=55.91/55.58, H=4.01/4.03, N=12.22/11.89

Example 5:

The following illustrate representative pharmaceutical dosage forms containing a compound of forlm-ula I, or a pharmaceutically acceptable salt thereof, for example as illustrated in any of the previous Examples, (hereafter referred to as "compound X"), for therapeutic or prophylactic use in humans:

| Ingredient | mg/tablet |
|---|---|
| (a) Tablet | |
| Compound X. | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule | |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coalting of cellulose acetate phthalate.

Example 6:

This is aln example of a formulation suitable for parenteral use made with the compound of Example 2:
(c) Parenteral Formulation:

| Ingredient | mg/mL |
|---|---|
| Compound | 10.0 |
| Meglumine | 19.5 |
| Dextrose, anhydrous | 39.5 |
| Sterile Water for Injection | qs ad 1 mL |

The solution may be prepared by conventional measures well known in the pharmaceutical field. General formulations for this class of compounds and their salts, may be prepared by solubilizing the active compound in an aqueous meglumine (N-methyl-glucamine) solution containing an equimolar, or if solubilization is difficult, a molar excess of meglumine relative to Compound. Choline salts are preferred for use in making formulations. Excipients such has dextrose may be added to adjust the osmolality of the formulation. Water for Injectilol)n is added to bring the solution to final volume. Alternately, other amine bases such as tromethamine or 1-arginine may be used to solubilize the active compound.

Example 7:

A formulation is made as in Example 6, except that the choline salt of Compound X is used in place of the compound of Example 2.

Example 8:

A formulation is made comprising a 5% aqueous solution of dextrose made to 10 mg/mL in the choline salt of Compound X.

The previous examples are considered to be non-limiting and thus, the compounds of formula I and phlarmaceutical compositions containing same may be used to treat and/or prevent stroke anld the other diseases as related herein.

We claim:
1. Any compound according to formula I, wherein:

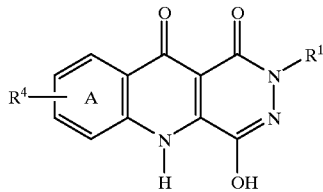

wherein:
$R^1$ is $(CH_2)_nL$, where n is an integer in the range 0 to 6 and L is a carbon-linked five-membered heteroaryl ring having an oxygen or sulfur heteroatom, and
$R^4$ at each occurrence is independently selected from hydrogen, halo and $NO_2$, and ring-A has four $R^4$ groups and pharmaceutically-acceptable salts thereof.

2. A compound or pharmaceutically-acceptable salts thereof according to claim 1, wherein:
$R^1$ is $CH_2L$ and L is selected from 2-linked or 3-linked furanyl or thiophenyl moieties.

3. A compcund or pharmaceutically-acceptable salts thereof according to claim 1, wherein:
$R^4$ is selected from hydrogen or halo, and ring-A has a 7-linked halo or 7,9-linked di-halo groups.

4. A compound or pharmaceutically-acceptable salts thereof according to claim 3, wherein:
$R^4$ is hydrogen or chloro, and ring-A has a 7-linked chloro or 7,9-linked di-chloro groups.

5. A compound according to claim 1, selected from:
7-chloro-4-hydroxy-2-(furan-2-ylmethyl)-1,2,5,10-tetrahydropyridazino[4,5-b]quinolin-1,10-dione;
7-chloro-4-hydroxy-2-(furan-3-ylmethyl)-1,2,5,10-tetrahydropyridazino [4,5-b]quinolin-1,10-dione;
7-chloro-4-hydroxy-2-(thiophen-2-ylmethyl)-1,2,5,10-tetrahydropyridazino[4,5-b]quinolin-1,10-dione, and
7-chloro-4-hydroxy-2-(thiophen-3-ylmethyl)-1,2,5,10-tetrahydropyridazino [4,5-b]quinolin-1,10-dione
or pharmiaceutically-acceptable salts thereof.

6. A pharmaceutically-acceptable salt comprising a compound according to claim 1, and at least one moilety selected from sodium, potassium, choline hydroxide, triethylamine, morpholine, piperidine, ethylenediamine, lysine, ethanolamine, diethanolamine, triethanolamine, N-methyl-D-glucamine, arginine, and tris(hydroxymethyl) aminomethane.

7. A pharmaceutical composition comprising a compound according to claim 1, and a pharmaceutically acceptable excipient or diluent.

8. A pharmaceutical composition comprising a pharmaceutically-acceptable salt according to claim 6, and a pharmaceutically acceptable excipient or diluent.

9. A method for the treatment of stroke, hypoglycemia, ischemic attack, anoxia and epilepsy which comprises administering to a patient in need of such treatment an effective amount of a compound according to claim 1.

* * * * *